United States Patent
Balanián et al.

(10) Patent No.: US 9,920,107 B2
(45) Date of Patent: Mar. 20, 2018

(54) PROCESS FOR OBTAINING HMG-UP (HUMAN MENOPAUSAL GONADOTROPIN WITH ULTRA-PURITY GRADE) AND A COMPOSITION FREE OF CONTAMINANTS

(71) Applicants: INSTITUTO MASSONE S.A., Buenos Aires (AR); Raul Enrique Massone, Buenos Aires (AR)

(72) Inventors: Liliana Balanián, Buenos Aires (AR); Mariana Cancela, Buenos Aires (AR); Claudio Wolfenson, Buenos Aires (AR); José Groisman, Buenos Aires (AR)

(73) Assignees: INSTITUTO MASSONE S.A., Buenos Aires (AR); RAUL ENRIQUE MASSONE, Buenos Aires (AR)

( * ) Notice: Subject to any disclaimer, the term of this patent is extended or adjusted under 35 U.S.C. 154(b) by 48 days.

(21) Appl. No.: 15/312,859

(22) PCT Filed: May 21, 2015

(86) PCT No.: PCT/IB2015/053745
§ 371 (c)(1),
(2) Date: Nov. 21, 2016

(87) PCT Pub. No.: WO2015/177751
PCT Pub. Date: Nov. 26, 2015

(65) Prior Publication Data
US 2017/0101453 A1     Apr. 13, 2017

Related U.S. Application Data

(60) Provisional application No. 62/002,671, filed on May 23, 2014.

(51) Int. Cl.
A61K 38/24 (2006.01)
C07K 14/59 (2006.01)
C07K 1/36 (2006.01)

(52) U.S. Cl.
CPC .............. *C07K 14/59* (2013.01); *A61K 38/24* (2013.01); *C07K 1/36* (2013.01)

(58) Field of Classification Search
None
See application file for complete search history.

(56) References Cited

U.S. PATENT DOCUMENTS 7,022,822 B1 * 4/2006 Wolfenson Band ... C07K 14/59
530/397

FOREIGN PATENT DOCUMENTS

WO    WO 00/63248       10/2000
WO    WO 2011/150110    12/2011

OTHER PUBLICATIONS

"Multimodal Chromatography—Handbook GE Healthcare Life Sciences Imagination at work Multimodal Chromatography Handbook" ((Nov. 2013) available at http://www.gelifesciences.com/webapp/wcs/stores/servlet/CategoryDisplay?categoryId=3304854&catalogId=10102&productId=&top=Y&storeId=11787&langId=-1; retrieved on Mar. 30, 2017).*
Burnouf et al., Haemophilia (2003) 9, 24-37.*
Birken S et al: "Preparation and Analysis of the Common Urinary Forms of Human Chorionic Gonadotropin". Methods. Academic Press. vol. 21 No. 1., May 1, 2000 (May 1, 2000). pp. 3-14. XP004466906. ISSN: 1046-2023. DOI: 10.1006/METH.2000. 0971, the whole document.
Van De Weijer B H et al: "Compositional analyses of a human menopausal gonadotrophin preparation extracted from urine (menotropin). Identification of some of its major impurities", Reproductive Biomedicine Online, Reproductive Healthcare Ltd. GB, vol. 7. No. 5, Jan. 1, 2003 (Jan. 1, 2003) pp. 547-557. XP027052221, ISSN: 1472-6483 [retrieved on Jan. 1, 2003], the whole document.
International Search Report, PCT/IB2015/053745, dated Aug. 4, 2015.
Bassett R et al.: "Analytical identification of additional impurities in urinary-derived gonadotrophins". Reproductive Biomedicine Online. Reproductive Healthcare Ltd. GB. vol. 19. No. 3. Jul. 9, 2009 (Jul. 9, 2009). pp. 300-313. XP009185530. ISSN: 1472-6483. The whole document.
"Multimodal Chromatography—Handbook GE Healthcare Life Sciences imagination at work Multimodal Chromatography Handbook" Dec. 17, 2013 (Dec. 17, 2013). XP055180446. Retrieved from the Internet: URL:https://www.gelifesciences.com/gehcls_images/GELS/Related-Content/Files/1384943366025/litdoc29054808201312202222224.pdf [retrieved on Mar. 31, 2015] the whole document.

* cited by examiner

*Primary Examiner* — Lianko G Garyu
(74) *Attorney, Agent, or Firm* — Young & Thompson

(57) ABSTRACT

The present invention refers to a method of purification of HMG (human menopausal gonadotropin) by multimodal chromatography in order to obtain HMG-UP (human menopausal gonadotropin with ultra-purity grade) composition.

2 Claims, 6 Drawing Sheets

Flow chart for obtaining ultra purified gonadotropins

References:
Lane 1: Ref Std FSH-HP, 1,4 mg/ml
Lane 2: Fraction J3, 1,4mg/ml
Lane 3: LMW std
Lane 4: J3-UP, 1,4 mg/ml References:
Lane 1: LMW GE Healthcare
Lane 2: HCG Ref Std, 2 mg/ml
Lane 3: Fraction J3-UP, 2mg/ml
Lane 4: Impurities fraction obtained from capto-adhere, 2mg/ml

PROCESS FOR OBTAINING HMG-UP (HUMAN MENOPAUSAL GONADOTROPIN WITH ULTRA-PURITY GRADE) AND A COMPOSITION FREE OF CONTAMINANTS

TECHNICAL FIELD

The present invention refers to a method of purification of HMG (human menopausal gonadotropin) by multimodal chromatography in order to obtain HMG-UP (human menopausal gonadotropin with ultra-purity grade) composition.

BACKGROUND OF THE INVENTION

The term "menotropins" is applied to a hormonal combination of gonadotropins obtained from menopausal and post-menopausal women's urine comprising two glycoprotein hormones: follicle stimulating hormone (FSH) and lutenizing hormone (LH); they are secreted by the pituitary gland, subsequently metabolized, and excreted in the urine.

Urinary gonadotropins have been used successfully to stimulate the ovaries in ovulation induction cycles or during assisted reproduction for several decades.

Since their introduction up to now, there have been significant improvements in manufacturing technology and purification processes. Due to the appropriate application of advanced technology in purification, it has become possible to obtain gonadotropins with a high purity grade, as for example HMG-HP.

European Patent EP1169349 B1 relates to gonadotropin compositions, particularly to FSH (follicle stimulating hormone: follitropin) and menotropin compositions of high biological activity and to a method for preparing these compositions from human crude urine of menopausal and postmenopausal women. The process disclosed by said European Patent EP1169349 B1 allows obtaining compositions of HMG-HP comprising potencies of FSH of 3700 IU/mg protein and 4300 IU/mg protein in examples 1 and 2 respectively of EP1169349 B1.

Despite these advances, urinary products still contains some non-gonadotropin proteins as contaminants (Bassett et al, Analytical identification of additional impurities in urinary-derived gonadotrophins 2009).

Some of the main contaminants of the gonadotropin HMG-HP composition comprise plasma serine protease inhibitor, afamin, insulin-like growth factor binding protein 7, zinc alpha-2-glycoprotein and albumin; all of them identified in the publication Bassett et al, 2009).

The challenge for improving the purification of urinary HMG-HP was to remove those proteins which co-purified with active principles but preserving the integrity of the FSH and LH bioactivities using a simple process with high yield.

To achieve this goal a new purification step was introduced to optimize the purification of HMG-HP of the prior art.

Briefly, during the HMG-HP manufacturing process as presented in the previous patent (European patent EP1169349 B1), two important fractions are obtained in the last chromatographic step (Hydrophobic interaction chromatography, HIC): one of them with FSH bioactivity (Fraction J2) and the other with LH bioactivity (Fraction J3).

Menotropin is a preparation that requires to have a FSH:LH bioactivity ratio of about 1:1.

To achieve a FSH:LH ratio of 1:1, there is a balance step to adjust the content of both hormones. In the case of HMG-HP, this balancing step is done by mixing FSH bioactivity from Fraction J2 with the LH bioactivity from Fraction J3.

As described in the current patent, Fraction J3 is usually contaminated with non-active proteins.

Therefore, to obtain the HMG-UP (HMG ultrapure) material without almost any detectable protein contamination, the LH bioactive fraction (Fraction J3) was successfully purified by multimodal chromatography, specifically a multimodal strong anion exchanger, Capto-adhere (Fraction J3-UP).

As it is well-known (ASRM Practice Committee; Fertility and Sterility, 90, Suppl. 3, S13, 2008) a small amount of hCG present in the preparation contributes to give the majority of the LH bioactivity of menotropin. Consequently, the purification of Fraction J3 implied the purification of the human chorionic gonadotropin (hCG) present in this fraction to obtain Fraction J3-UP.

Finally, to produce HMG-UP, the balancing step involved in this case mixing in equivalent amount the FSH bioactivity from Fraction J2 with LH bioactivity from the now much more purified Fraction J3-UP instead of the previous more contaminated Fraction J3.

For obtaining a composition of HMG-UP, the solution obtained after the balancing step is subjected to the steps of sterile filtration, nanofiltration and precipitation.

SUMMARY OF THE INVENTION

The present invention comprises a process for obtaining HMG-UP (human menopausal gonadotropin with ultra-purity grade) composition free of non-related gonadotropin contaminants, wherein
  a gonadotropin composition contaminated with serine protease inhibitor, afamin, insulin-like growth factor binding protein 7, zinc alpha-2-glycoprotein and albumin is subjected to the following steps:
    i) purification of the said gonadotropin contaminated using a strong anion exchanger with multimodal functionality, eluting with a buffer at a constant pH but modifying the conductivity obtaining a Fraction J3-UP which only has LH activity;
    ii) obtaining HMG-UP by a balancing step by mixing in equivalent amounts the FSH bioactivity from Fraction J2 with LH bioactivity from Fraction J3-UP;
    iii) subjecting said solution of HMG-UP to the steps of:
      1) sterile filtration,
      2) nanofiltration, and
      3) precipitation;
  in order to obtain a HMG-UP (human menopausal gonadotropin with ultra-purity grade) composition free of non-related gonadotropin protein contaminants such as protease inhibitor, afamin, insulin-like growth factor binding protein 7, zinc alpha-2-glycoprotein and albumin.

In the process for obtaining HMG-UP (human menopausal gonadotropin with ultra-purity grade) composition by removal of plasma serine protease inhibitor, afamin, insulin-like growth factor binding protein 7, zinc alpha-2-glycoprotein and albumin indicated above, the Fraction J3-UP is obtained from human menopausal/postmenopausal urine.

An embodiment preferred of the invention comprises a process for obtaining HMG-UP (human menopausal gonadotropin with ultra-purity grade) composition by removal of inactive non-gonadotropin proteins such as plasma serine protease inhibitor, afamin, insulin-like growth factor binding protein 7, zinc alpha-2-glycoprotein and albumin comprising the steps of:

i) performing an initial treatment of an acidified human menopausal/postmenopausal urine with kaolin wherein proteins including gonadotropins present in urine are adsorbed to the kaolin;

ii) eluting the gonadotropins adsorbed in kaolin by alkaline elution;

iii) precipitating the alkaline elution with acetone for obtaining the Fraction A;

iv) extracting the bioactive fraction from this precipitate Fraction A with 10% w/v solution of ammonium acetate in ethanol (70%) and precipitated with 10% ammonium acetate in ethanol (90%) to obtain Fraction B;

v) performing a purification of the Fraction B by ion-exchange chromatography for obtaining the Fraction C (HMG Source Material or equivalent);

vi) performing a purification of the Fraction C by cation exchange chromatography using a strong cationic resin, eluting with ammonium acetate;

vii) precipitating in acid medium obtaining a Fraction F from the eluted obtained above;

viii) purification of the Fraction F by anion exchange chromatography using a strong anionic resin, eluting with ammonium acetate for the obtaining of the Fraction G;

ix) purification of the gonadotropins obtained in Fraction G using hydrophobic interaction chromatography by sequential addition of buffers which contain decreasing concentration of ammonium sulfate to obtain Fractions J2 and J3 wherein Fraction J2 has mostly FSH bioactivity and Fraction J3 has LH bioactivity;

x) purification of the gonadotropin of Fraction J3 using a strong anion exchanger with multimodal functionality, eluting with a buffer at a constant pH but modifying the conductivity obtaining a Fraction J3-UP which only has LH bioactivity;

xi) obtaining of a HMG-UP in a balancing step by mixing of equivalent activities of FSH in Fraction J2 and LH in Fraction J3-UP;

xii) subjecting said HMG-UP solution to the steps of:
   4) sterile filtration,
   5) nanofiltration, and
   6) precipitation;

in order to obtain a HMG-UP (human menopausal gonadotropin with ultra-purity grade) composition free of non-related gonadotropin protein contaminants such as protease inhibitor, afamin, insulin-like growth factor binding protein 7, zinc alpha-2-glycoprotein and albumin.

In the preferred embodiment of the process for obtaining HMG-UP (human menopausal gonadotropin with ultra-purity grade) composition the Fraction J2 can be subjected to an additional step purification using a strong anion exchanger with multimodal functionality, eluting with a buffer at a constant pH but modifying the conductivity obtaining an ultra pure fraction which only has FSH bioactivity (Fraction J2-UP) which is subjected to the balancing step by mixing it with LH bioactivity present in the Fraction J3-UP.

DETAILED DESCRIPTION OF THE INVENTION

Figure 1:
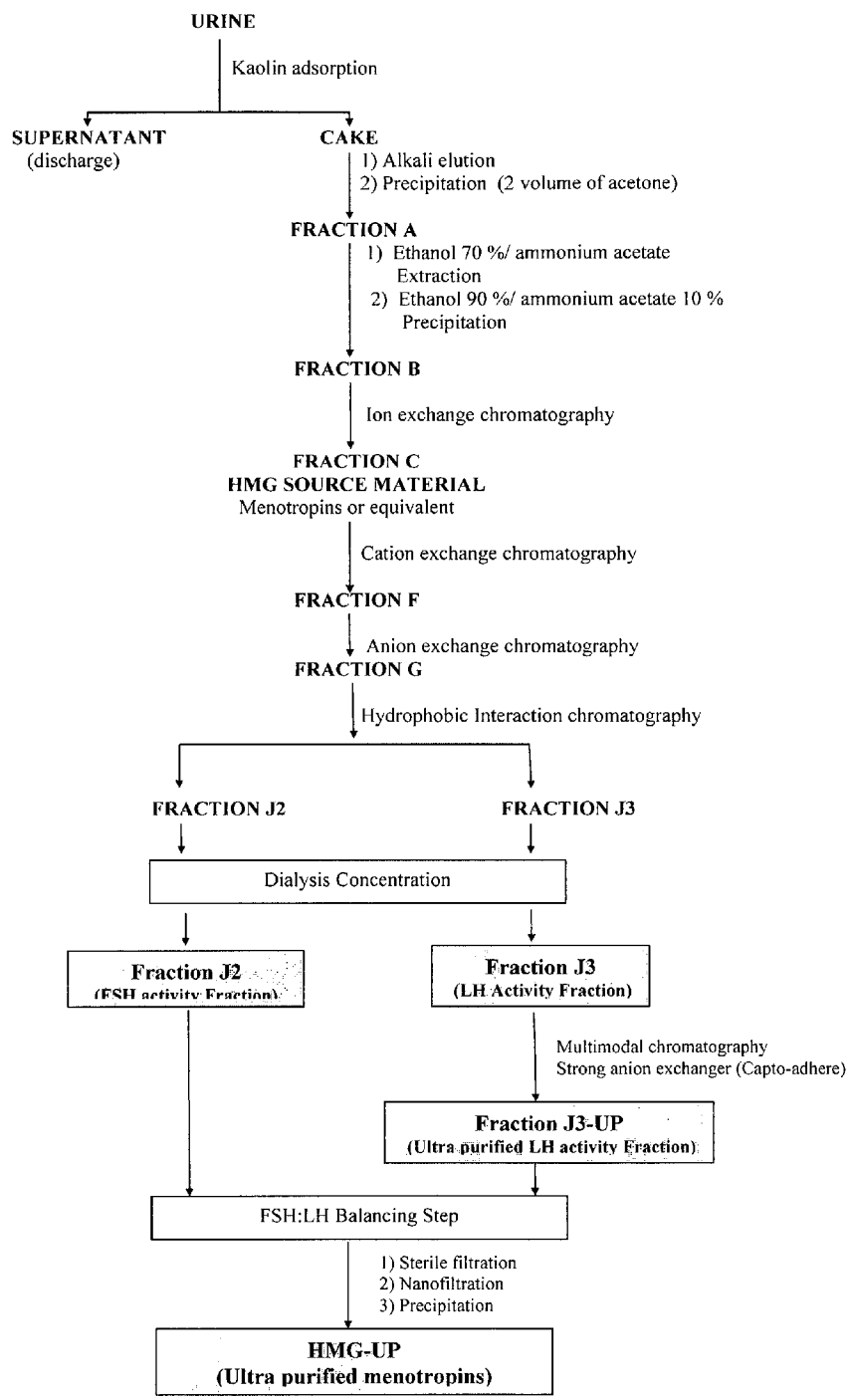
FIG. 1: shows the Flowchart for obtaining HMG-UP of present application.

The study presented in this application shows that it is possible to obtain an HMG ultra pure with a purity superior to HMG-HP by adding one more new chromatographic step to the existing manufacturing process.

This new step consists in the removal of impurities which co-eluted with LH fraction by Mixed-Mode chromatography using specifically a multimodal strong anion exchanger.

Mixed Mode or Multimodal Chromatography Supports:

Mixed-Mode or Multimodal Chromatography refers to chromatography that substantially involves a combination of two or more interaction mechanisms between the ligands and the target molecules. In some embodiments, the combination results in unique selectivity such that it is able to achieve fractionation of antibodies that cannot be achieved by a single mode support. In certain embodiments, the mixed-mode resin comprises a negatively charged part and a hydrophobic part. In one embodiment, the negatively charged part is an anionic carboxylate group or an anionic sulfo group for cation exchange. Examples of such supports include, but are not limited to, Capto-MMC™ (GE Healthcare).

Various other mixed mode chromatography media are available commercially such as Carboxy-Sulfon™ fluoro-apatite (CFT), MEP-Hypercel™, Capto-Adhere™, Bakerbond™, and Bakerbond™ ABx™.

It is more specifically used as embodiment of the present invention, the Capto-adhere ligand, N-Benzyl-N-methyl ethanol amine, which exhibits many functionalities for interaction. The most pronounced are ionic interaction, hydrogen bonding and hydrophobic interaction. The ligand is coupled to a chemically modified, high flow agarose matrix. The agarose matrix provides particle rigidity without compromising the pore size.

These properties of the agarose matrix allows for fast mass transfer, resulting in high dynamic binding capacities of Capto-adhere at high flow.

The highly cross-linked agarose base matrix gives the medium high chemical and physical stability.

Materials and Methods:

Source of Material:

The LH activity from Fraction J3 was obtained as described in the European patent EP1169349 B1 by HIC (hydrophobic interaction chromatography).

Fraction J3 was dialyzed against buffer 40 mM tris pH 8.5 and then concentrated by Amicon cell, using polyethensulfone filter Code PM10, cut off 10000 Cat N° 13122 (Millipore).

The protein content of the sample was 75 mg of protein/ml of solution

Multi ModalChromatography:

Multi Modalchromatography was performed using an ÄKTA Purifier system.

Column XK 16/40 was prepared with Capto-adhere Code N° 17-5444-99 following instructions of the insert.

Properties of Capto-Adhere:

This resin is mainly recommended for contaminant removal in post Protein A steps to eliminate dimers and aggregates during the manufacturing of antibodies and also host cell proteins and nucleic acids.

Capto-adhere is a strong anion exchanger with multi-modal functionality. The multimodal functionality gives a different selectivity compared to traditional anion exchangers.

The Capto-adhere ligand, N-Benzyl-N-methyl ethanol amine, exhibits many functionalities for interaction. The most pronounced are ionic interaction, hydrogen bonding and hydrophobic interaction. The ligand is coupled to a chemically modified, high flow agarose matrix.

The agarose matrix provides particle rigidity without compromising the pore size.

These properties of the agarose matrix allow for fast mass transfer, resulting in high dynamic binding capacities of Capto-adhere at high flow.

The highly cross-linked agarose base matrix gives the medium high chemical and physical stability.

In this patent, the multimodalchromatography was performed at room temperature, at a flow rate of 3 ml/min and the mode of elution selected was bind-elute.

The elution was done keeping the pH constant but modifying the conductivity of the buffer.

A 40 mM tris buffer at pH 8.5 was selected and a gradient in steps was done using NaCl.

LH bioactivity was eluted at low conductivities. On the other hand, contaminants were desorbed at high conductivities.

Detection was carried out at 280 nm.

Summary of Chromatographic Conditions Selected:
Column XK 16/40: Volume 24 ml.
Load: 50 mg of protein of LH activity fraction Lot 4625/51-1.
Flow: 3 ml/min
Detection: 280 nm
Buffers of elution:
40 mM tris buffer at pH 8.5+0 mM NaCl
40 mM tris buffer at pH 8.5+50 mM NaCl
40 mM tris buffer at pH 8.5+100 mM NaCl
40 mM tris buffer at pH 8.5+225 mM NaCl
40 mM tris buffer at pH 8.5+300 mM NaCl
40 mM tris buffer at pH 8.5+1000 mM NaCl Analytical Methods:

Total Protein Content:

Total protein content was determined according to the method of Lowry [Lowry et al 1951] as modified by Hartree [Hartree, 1972]. Bovine Serum Albumin was used as standard.

Bioassay:

The LH and FSH bioactivity of the samples was evaluated using in vivo bioassay.

a) Biological Assay of Follicle-Stimulating Hormone (FSH)

Method: Ovaries weight augmentation method (USP XXXV, British Pharmacopeia 2015, volume III).

Primary Reference Standard: International Standard for Urinary FSH and Urinary LH (NIBSC, WHO-ECBS).

Working Reference Standard: Menotrophins (HMG) manufactured by Instituto Massone S. A., calibrated against the Primary Reference Standard.

Animals: Female rats from the Wistar strain, 21-24 days old, in groups of 6 animals per cage with weights differing in not more than 10 grams within the group.

Doses: 3×3 test, i.e., 3 doses of the working standard and 3 doses of the sample, one dose tested per cage. Low dose: 2.4 IU; Medium dose: 4.3 IU; High dose: 7.7 IU.

Buffer: Phosphate-albumin buffered saline pH 7.2 containing 28 IU hCG/ml.

b) Biological Assay of Luteinizing Hormone (LH)

Method: Seminal vesicle weight augmentation method (USP XXXV, British Pharmacopeia 2015, volume III).

Primary Reference Standard: International Standard for Urinary FSH and Urinary LH (NIBSC, WHO-ECBS).

Working Reference Standard: Menotrophins (HMG) manufactured by Instituto Massone S. A., calibrated against the Primary Reference Standard.

Animals: Male rats from the Wistar strain, 21-24 days old, in groups of not less than 6 animals per cage with weights differing in not more than 10 grams within the group.

Doses: 3×3 test, i.e., 3 doses of the working standard and 3 doses of the sample, one dose tested per cage. Low dose: 7 IU; Medium dose: 14 IU; High dose: 28 IU.

Buffer: Phosphate-albumin buffered saline pH 7.2.

SDS-PAGE:

The different fractions were characterized by SDS-PAGE under reductive conditions as described in the PhastSystem User manual (File N° 110).

Samples were taken up in sample buffer with reducing agent and heated for 5 min at 95-100° C.

Silver staining was used to visualize the protein profile.

All the materials used to perform the SDS-PAGE can be summarized as follows:

Electrophoresis separation was done using: PhastSystem (GE Healthcare).
Image of the gels were processed using ImageScanner (PowerLook 1120 "UMAX") with Software LabScan 5.0, GE Healthcare. Image Quant TL version 2005, Amersham Biosciences.
Sample applicator 8/1 (1 µl), GE Healthcare Code N° 18-1618-01.
LMW calibration mixture from GE Healthcare Code N° 17-0446-01.
HMG HP reference standard.
HCG HP reference standard.
Phastgel gradient 8-25% SDS GE Healthcare Code N° 17-0542-01.
Buffer system in the gels: 0.112 M acetate (leading ion) and 0.112 M Tris, pH 6.5.
Phastgel SDS Buffer strips 2-3% agarose GE Healthcare Code N° 17-0516-01.
TRIS/HCl p.a.
EDTA-$Na_2$ p.a.
β-Mercaptoethanol p.a.
Sample buffer: 10 mM Tris/HCl, 1 mM EDTA, pH 8.0+2.5% SDS, +5% beta-mercaptoethanol+0.01% bromophenol blue.

Two-Dimensional Electrophoresis:

Samples of HMG-UP and HMG-HP, and the intermediates Fraction J3 and Fraction J3-UP were further characterized by a very sensitive technique as two-dimensional electrophoresis that is able to separate the sample according to both the molecular weight of the different species present in the preparation and also by their pI.

In fact, proteins were separated on a first dimension according to their isoelectric point (pI) and then on a second dimension according to their molecular weight.

Samples were prepared in IEF-buffer (7 M urea, 2 M Tiourea, 2% CHAPS, 2% Triton X-100, 20 mM DTT, 1% w/v carrier ampholytes pH 3-10). Protein content was determined by Bradford method.

IPG strips (7 cm pH 3-10) were rehydrated overnight with 125 µl f IEF buffer containing 200 µg of protein.

First dimension gels were run in an Ettan IPGphor 3 IEF System (GE Healthcare) at 20° C. with steps of 500V for 30 min, 1000V for 30 min, and 5000V for 1 h 40 min.

After focusing, the proteins were reduced by incubating the IPG strips with 4 ml of equilibration buffer (EB; 50 mM Tris-HCl pH 8.8, 6M urea, 30% glycerol, 2% SDS and 0.01% bromophenol blue) and 1% w/v DTT during 1 h a RT. Immediately, the proteins were alkylated with 5.5% w/v iodoacetamide in 4 ml of equilibration buffer for 1 h.

Electrophoresis in the second-dimension was carried out on 15% polyacrylamide gel.

Following 2D separation the gels were stained by silver or Coomassie blue staining.

Gels were scanned using Image Scanner III (GE Healthcare). The quantification of protein spots was carried out using the software Image Master 2D Platinum version 7.0.

Proteomic Map

Spots of samples obtained by two-dimensional electrophoresis were analyzed by MALDI-TOF MS and identified from databases.

For MALDI-TOF MS analysis proteins were in-gel digested with trypsin (sequence grade, Promega) as previously described [Hellman, 2000].

Peptides were extracted from gels using aqueous 60% acetonitrile (ACN) containing 0.1% TFA and concentrated by vacuum drying. 1 ul of peptide mixture was mixed with 1 ul matrix solution (α-cyano-4-hydroxycinnamic acid in 60% ACN containing 0.1% TFA) onto the MALDI sample plate. Mass spectra of peptides mixtures were acquired in a 4800 MALDI TOF/TOF instrument (ABi Sciex) in positive reflector mode and were externally calibrated using a mixture of peptide standards (Applied Biosystems). Collision-induced dissociation MS/MS spectra of selected peptides ions were acquired.

Proteins were identified with measured m/z values in MS and MS/MS acquisition modes and using the MASCOT search engine (Matrix Science, http://www.matrixscience.com). (The search parameters for each individual search are included in the report of results).

Significant protein scores (p<0.05) and at least one peptide ion significant score (p<0.05) per protein were used as criteria for positive identification.

Results

Production of Fraction J3-UP by MultimodalChromatography:

Multimodal Chromatography was performed using a strong anion exchanger. Capto-adhere was used to purify the LH bioactivity present in the Fraction J3 that was obtained by hydrophobic interaction chromatography (HIC). 50 mg of Fraction J3 was loaded onto XK 16/40 column prepared with Capto-adhere (Vol 24 ml) using an ÄKTA purifier system. Gradient in different steps was used to eliminate impurities.

Figure 2:
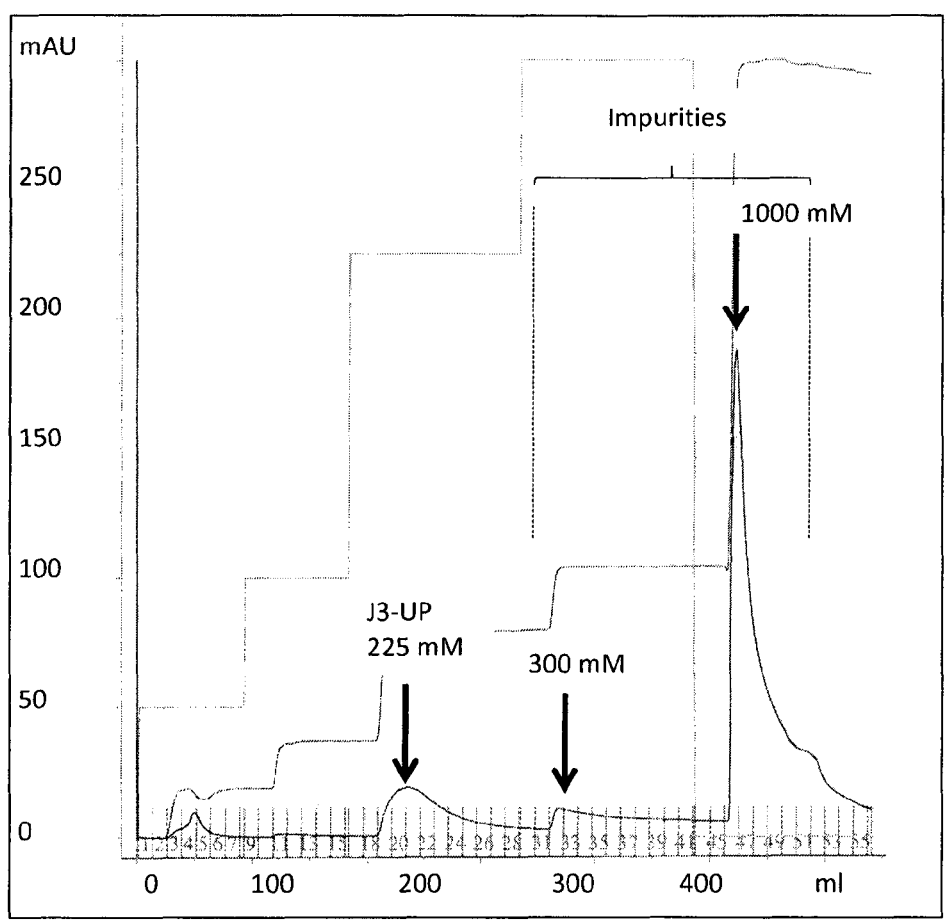
FIG. 2: shows the obtaining of Fraction J3-UP by Multimodal Chromatography using Capto-adhere.

The sequence of buffers used were:
   40 mM tris buffer at pH 8.5+0 mM NaCl
   40 mM tris buffer at pH 8.5+50 mM NaCl
   40 mM tris buffer at pH 8.5+100 mM NaCl
   40 mM tris buffer at pH 8.5+225 mM NaCl
   40 mM tris buffer at pH 8.5+300 mM NaCl
   40 mM tris buffer at pH 8.5+1000 mM NaCl Purified LH fraction (Fraction J3-UP) was obtained with 40 mM tris buffer at pH 8.5+225 mM NaCl buffer (FIG. 2). As in FIG. 2, the major area under the curve of the chromatogram corresponds to LH inactive protein that elutes late in the chromatography when a high molarity buffer (1000 mM NaCl) is used. The LH bioactivity that is recovered in a small protein peak eluted with 225 mM NaCl strongly suggests a high purification achievement. The specific LH bioactivity was determined by bioassay (see Table 1).

The biological analysis for LH bioactivity performed on Fractions J3-UP is shown below. For comparative purpose the biological analysis done on the starting material, Fraction J3, is presented as well in Table 1.

TABLE 1

| Fraction | LH Specific Biopotency (IU LH/mg protein) | Purification |
|---|---|---|
| J3-UP | 58,300 | More than 6 |
| J3 | 9,400 | times |

The yield of the process determined by the LH biopotency recovered in the J3-UP fraction was about 80%.

Figure 3:
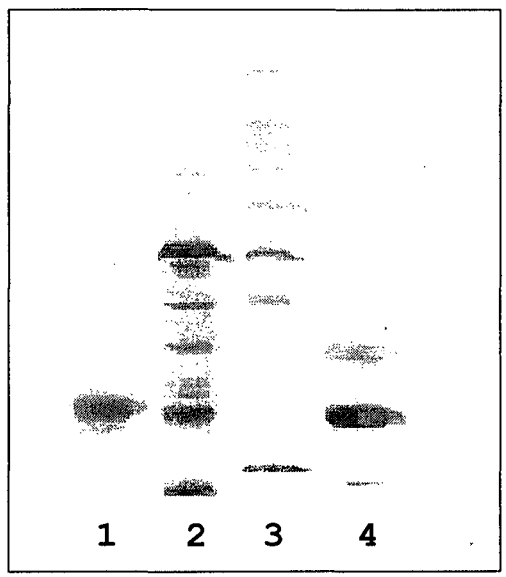
FIG. 3: shows the characterization of Fraction J3-UP by SDS-PAGE (sodium dodecyl sulfate-Polyacrylamide gel electrophoresis).
Figure 4:
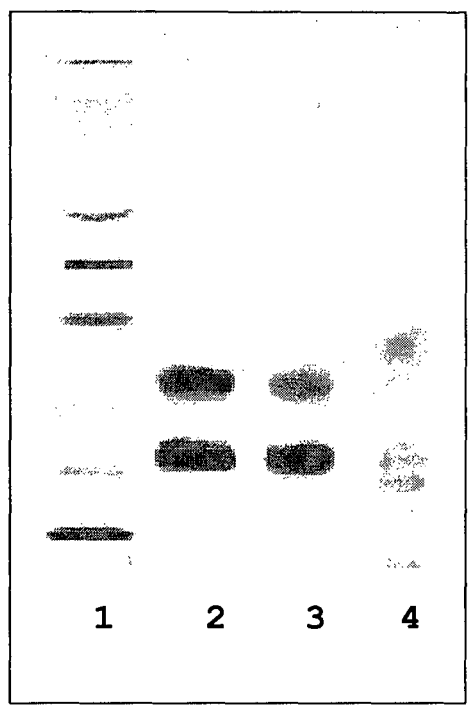
FIG. 4: shows the characterization of Fraction J3-UP by SDS-PAGE (sodium dodecyl sulfate-Polyacrylamide gel electrophoresis).
Figure 5:
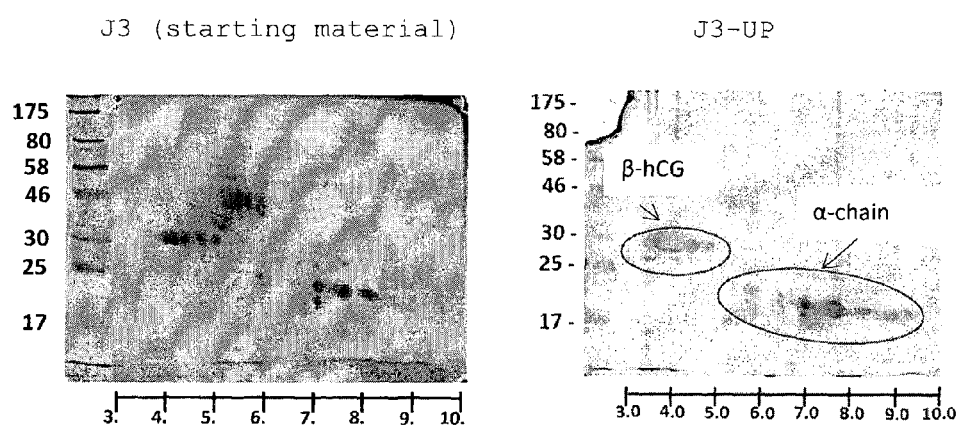
FIG. 5: shows the characterization of Fraction J3 and Fraction J3-UP by 2D gel. Identification of alpha and beta hCG was performed by MALDI-MS (Matrix-Assisted Laser Desorption/Ionization-Mass Spectrum).

Fraction J3-UP was further characterized by SDS-PAGE (Polyacrylamide gel electrophoresis) and also by two-dimensional electrophoresis (FIGS. 3, 4 and 5).

SDS-PAGE:

The protein pattern of Fraction J3 and Fraction J3-UP were analyzed on a 8-25% gel in reducing conditions and silver stained.

As shown in FIG. 3, Fraction J3 is a very impure fraction (Lane 2). Fraction J3 was successfully purified by the Capto-adhere. In fact, a very clean fraction, Fraction J3-UP was obtained (Lane 4). Fraction J3-UP has a typical electrophoretic pattern that corresponds to hCG (FIG. 4, Lanes 2 and Lane 3). In fact, the 2 bands that appear in the SDS-PAGE of Fraction J3-UP correspond to the alpha and the beta chain of hCG.

Two-Dimensional Electrophoresis

Analysis of the purified material Fraction J3-UP (FIG. 2) by two-dimensional electrophoresis shows that Capto-adhere is capable to rend a product with only the spots corresponding to alpha and beta hCG (FIG. 5) as determined by MALDI MS Matrix-Assisted Laser Desorption/Ionization Mass Spectrum. On the hand, the high amount of impurities present in the starting material (Fraction J3) makes even difficult to assign the bands corresponding to the active (alpha and beta hCG).

Preparation HMG-UP

The Fraction J3-UP purified by Capto-adhere containing the LH bioactivity was used in the balancing step to adjust the FSH and LH activities in a ratio of about 1:1 to obtain HMG-UP. This balancing step was done by mixing equivalent amount of the FSH activity from Fraction J2 with LH bioactivity from Fraction J3-UP.

Fractions J2 and J3-UP were defrozen and mixed in an amount of approximately 10,000 IU FSH and LH respectively to obtain a preparation of about 1:1.

The FSH and LH biological activity of the HMG-UP was determined as shown below. Results for HMG-HP are shown for comparative purposes.

TABLE 2

| Product | FSH Specific Biopotency (IU FSH/mg protein) | LH Specific Biopotency (IU LH/mg protein) | Purification |
|---|---|---|---|
| HMG-UP | 8,300 | 8,200 | About 175% more pure |
| HMG-HP | 4,800 | 4,600 | |

Although the method used in European Patent EP1169349 B1 allows obtaining compositions of HMG-HP comprising potencies of FSH of 3700 IU/mg protein and 4300 IU/mg protein respectively (see Examples 1 and 2), the method described in the current patent obtains a value above of 8000 IU/mg protein for both hormones (FSH and LH).

As can be observed, HMG-UP has a substantial higher FSH and LH biopotency than the HMG-HP.

Characterization of HMG-UP by Two-Dimensional Electrophoresis

HMG-UP was further characterized by two-dimensional electrophoresis. This technique is very sensitive and has excellent resolution. In fact, it is able to separate proteins according to their isoelectric points in one dimension and according to their molecular weights in the second one. Both HMG-UP and HMG-HP were run for comparative purposes.

Figure 6:
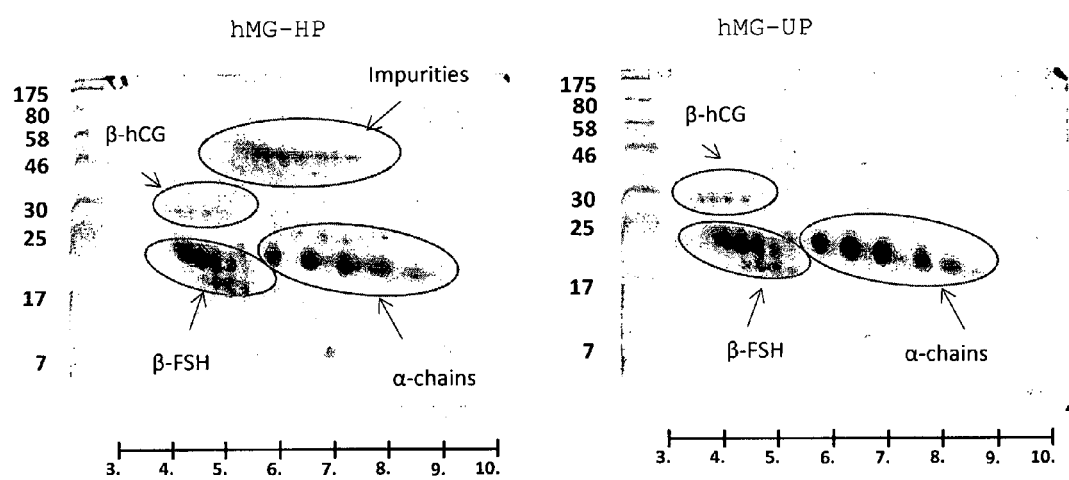
FIG. 6: shows the characterization of HMG-HP and HMG-UP by 2D gel. Identification of the different spots was performed by MALDI-MS (Matrix-Assisted Laser Desorption/Ionization-Mass Spectrum).

The Results obtained can be observed in FIG. 6.

As shown in FIG. 6, in the HMG-HP material, the two-dimensional electrophoresisis able to detect impurities eluting at a molecular weight of about 45,000. This spots are absent in the HMG-UP confirming the higher purity grade of this preparation. According to both MALDI-TOF MS identification and literature data (Bassett, 2009; Kuwabara, 2009) the other shared spots correspond to the bioactive proteins of the gonadotrophin preparation: beta HCG (MW about 27,000), beta FSH (MW about 20,000) and the common alpha FSH/HCG chain (MW about 17,000). The two-dimensional electrophoresis confirms that the impurities were successfully removed by the Capto-adhere chromatography.

MALDI-TOF MS identification of the non-gonadotropin proteins indicated that the majority of the impurities that were removed correspond to plasma serine protease inhibitor.

Finally, protemics studies were also performed to characterize the impurities that were removed during the Capto-adhere chromatography. To increase the sensitivity of the identification, the impurity-enriched 300 mM NaCl and 1000 mM NaCl fractions of the Capto-adhere purification (FIG. 2) were analyzed by two dimensional gel electrophoresis followed by mass spectrometry. The major impurities that were removed besides plasma serine protease inhibitor were afamin, insulin-like growth factor binding protein 7, zinc alpha-2-glycoprotein and albumin. This non-gonadotropin contamination pattern is in line with the published data [Bassett; 2009; van der Weijer 2003]. All these impurities are undetectable in Fraction J3-UP and in the final HMG-UP product.

Preferred Embodiment

As preferred embodiment of the present invention showed in in the flow chart of FIG. 1, considering the common steps disclosed in EP1169349 B1; said embodiment is performed as follow:

The starting material, from now on the "HMG source material", that can be used in the present invention for obtaining ultra-purified menotropins, constitutes the menotropins specialty, as specified in the pharmacopoeias (USP XXXV, British Pharmacopeia 2015, volume III) or any other material closely related to this specialty as it has been disclosed in the European Patent EP 1169349 B1. Therefore it is understood that this preparation process is also applicable to other materials that do not strictly meet the requirements applicable to menotropins. In fact, satisfactory results were obtained using Fraction C obtained in the Examples of in the European Patent EP 1169349 B1.

Moreover, the present invention provides a procedure to adjust the FSH:LH ratio when needed being therefore capable of providing ultra-purified menotropins specialty even when starting materials which are out of the correct FSH:LH ratio are used. Thanks to this, it is possible to obtain a product comprised of FSH and LH in the appropriate ratio 1:1 necessary to produce the pharmaceutical preparation. The steps described in the present invention can be used following in a different order from the one herein described, which does not imply varying the invention philosophy. Equally satisfactory results were obtained by inserting, for example, the hydrophobic interaction resin between the two ionic exchange chromatography steps described later.

Urine, the starting material used the present invention for producing ultra-purified menotropins is essentially obtained by a very well known method which employs kaolin to adsorb gonadotropins from the menopausal/postmenopausal urine (BP 1980). Briefly, bioactive fraction is extracted from the acidified urine with kaolin, eluted with alkali and precipitated with 2 volumes of acetone. Then, the bioactive fraction is extracted from this precipitate with 10% w/v solution of ammonium acetatein ethanol (70%) and precipitated with 10% ammonium acetate in ethanol (90%). Further purification is done by ion-exchange chromatography. The purified material obtained by this process constitutes the menotropins composition or some other equivalent preparation, like Fraction C obtained in the European Patent EP 1169349 B1.

Steps of Purification 1) purification of said gonadotropins crude diluted in 0.05-0.15 M ammonium acetate, pH 5.0-6.0. in an ionic exchange column with a strong cationic resin of the type of sulphopropyl, eluting both FSH and LH biactivities with solutions of 0.05-0.5 M ammonium acetate, pH 5.0-7.0; and 2) purification of this fraction diluted in 0.01-0.05 M ammonium acetate, pH 5.0-7.0 in a column of ionic exchange with a strong anionic resin of the ammonium quaternarium type, eluting both FSH and LH with solutions of 0.05-0.2 M ammonium acetate, pH 5.0-7.0; and 3) purification of gonadotropins in a column with an hydrophobic interaction resin by the sequential addition of the following solutions: a) buffer of 50-200 mM sodium phosphate, and 0.8-1.2 M ammonium sulfate, pH 5.0-6.0 (impurities); b) buffer of 50-200 mM sodium phosphate, and 0.4-0.6 M ammonium sulfate; pH 5.0-7.0 (Fraction J2) and c) buffer of 50-200 mM sodium phosphate (50-70% v/v), and ethanol 96% (50-30% v/v) (Fraction J3).

4) purification of gonadotropin Fraction J3 with a strong anion exchanger with multimodal functionality. The elution was done keeping the pH constant but modifying the conductivity of the buffer. A 40 mM tris buffer at pH in a range of 7 to 10, preferably pH 8.5, was selected and a gradient in steps was done using NaCl. LH bioactivity was eluted at low conductivities. On the other hand, contaminants were desorbed at high conductivities.

Resins of the type of SP-Sepharose, Q-Sepharose and hydrophobic interaction resins may be used in these steps. A preferred hydrophobic interaction resin is a Phenyl-Sepharose resin and multimodal resin is a Capto-adhere.

The process of the invention further comprises secondary steps of precipitation, centrifugation, ultrafiltration, dialysis, washing, drying in vacuo, and cooling. Description of the method:

Preparation of Fraction F:

Fraction C is chromatographed on a chromatographic column containing 10 liters of strong cationic exchange resin of the sulphopropyl type.

Fraction C (110-140 g) is dissolved in 1600-1800 ml of a 0.05-0.15 M ammonium acetate solution, pH 5.0-7.0. The column is run and eluted with the necessary amount of 0.05-0.15 M ammonium acetate solution to bring the volume to 20 liters. The elution is continued with solutions of 0.15-0.20 M ammonium acetate, pH 5.0-7.0 (20 liters) and 0.2-0.5 M ammonium acetate, pH 5.0-7.0 (20 liters). The active fraction eluted with the latter solution is added with stirring to 4 volumes of 96% ethanol and enough acetic acid to reach a mixture pH of 5.5-5.7. A precipitate is formed, separated by centrifugation, washed with ethanol and dried in vacuo until ethanol is removed and humidity is lower than 5% (Fraction F).

Preparation of Fraction G

Fraction F is chromatographed on a chromatographic column containing 4 liters of strong anionic exchange resin of ammonium quaternary type.

Fraction F (40-60 g in 650 ml) is dissolved in 0.01-0.05 M ammonium acetate solution, pH 5.0-7.0, the column is run and eluted with the same solution to brine the volume to 7 liters. Elution is continued with 12 liters of 0.05-0.07 M ammonium acetate. pH 5.0-7.0. Then with 10 liters of 0.07-0.2 M ammonium acetate. pH 5.0-7.0. The active fraction eluted with the latter solution is subjected to an ultrafiltration process using a PM 10 (10000 D) Ultrafilters (Amicon-Millipore) membrane. The solution is concentrated and dialyzed against 50 mM sodium phosphate buffer, pH 5.5-5.7 to a concentration of 2-4 g of protein in 100-150 ml of buffer. Then it is frozen at −75° C. (Fraction G).

Preparation of Fractions J

Fraction G is chromatographed on a chromatographic column containing 400 ml of a hydrophobic interaction resin (Phenyl Sepharose HP, Amersham-Pharmacia Biotech).

A sufficient amount of ammonium sulfate is added to the solution of Fraction G to obtain a 0.8-1.2 M concentration.

Put the solution of Fraction G in the chromatographic column.

Elute with 2 volumes of 50-200 mM sodium phosphate buffer, 0.8-1.2 M ammonium sulfate, pH 5.0-7.0.

Continue the elution with 2 volumes of 50-200 mM sodium phosphate buffer, 0.4-0.6 M ammonium sulfate, pH 5.0-7.0 and finally with 2 volumes of 50-200 mM phosphate buffer (50-70% v/v) and 96% ethanol (50-30% v/v).

The active fraction eluted with 50-200 mM sodium phosphate buffer, 0.4-0.6 M ammonium sulfate (Fraction J2) is frozen at −75° C. This fraction has mostly FSH activity.

The active fraction eluted with 50-200 mM phosphate buffer (50-70% v/v) and 96% ethanol (50-30% v/v) (Fraction J3) is frozen at −75° C. This fraction only has LH bioactivity.

Preparation of Fraction J3-UP

Fraction J3 is chromatographed on a chromatographic column containing 24 ml of a strong anion exchanger with multimodal functionality (Capto-adhere, GE). A 40 mM tris buffer at pH 7 to 10, preferably pH 8.5, was selected and a gradient in steps was done using NaCl.

LH bioactivity was eluted at low conductivities. On the other hand, contaminants were desorbed at high conductivities. A stepwise elution was performed using lower than 30 mM, preferably 0 mM; 30 mM to 75 mM, preferably 50 mM; 75 mM to 180 mM, preferably 100 mM; 180 mM to 250 mM, preferably 225 mM; 250 mM to 700 mM, preferably 300 mM and 700 mM to 1500 mM, preferably 1000 mM NaCl in 40 mM tris buffer at pH 7 to 10, preferably pH 8.5.

LH bioactive fraction (J3-UP) was eluted with 225 mM NaCl.

Fraction J3-UP is frozen at −75° C. This fraction only has LH bioactivity.

Balancing Step:

HMG-UP is obtained by mixing equivalents activities of FSH (Fraction J2) and LH (Fraction J3-UP) to have a 1:1 ratio of both hormones.

Examples of Batches Produced by the Described Technique 1.1 Preparation of Fraction F 231.2 g of Fraction C were divided m two equal portions and chromatographed in two equivalent processes on a chromatographic column as above described.

115.6 g of Fraction C (in each process) were dissolved in 1700 ml of 0.05 M ammonium acetate buffer, pH 5.0 The column was run and eluted with further 18.7 liters of the same chromatographic buffer. The elution was continued with 20 liters of 0.15 M ammonium acetate buffer, pH 5.0 and finally with 20 liters of 0.5 M ammonium acetate buffer, pH 5.0 The active fraction obtained by eluting with 0.5 M ammonium acetate (22 liters) was added with stirring to a solution of 88 liters of 96% ethanol and 2400 ml of acetic acid. The pH of the mixture was 5.7. The precipitate obtained was left in the refrigerator (2-8° C.) overnight. The precipitate was centrifuged, washed with 96% ethanol and dried in vacuo for 17 h.

On each of the two equivalent processes, two Fractions F of 20.7 g and 19.5 g were obtained, respectively.

1.2 Preparation of Fraction G

The two fractions F obtained in the above step were brought together and chromatographed on column according to the described technique.

40.2 g of Fraction F were dissolved in 650 ml of 0.01 M ammonium acetate buffer, pH 5.0. The column was run with this solution and eluted with 6350 ml of the same dilution buffer. The elution was then continued with 12 liters of 0.05 M ammonium acetate, pH 5.0 and then with 10 liters of 0.2 M ammonium acetate, pH 5.0. The active fraction (4500 ml) eluted with the latter solution was subjected to an ultrafiltration process using a PM 10 (10000 D) Diaflo Ultrafilters (Amicon-Millipore) membrane. The solution is concentrated and dialyzed against 50 mM sodium phosphate, pH 5.7 for obtaining a concentration of 2-4 g of protein in 150 ml of buffer. Final solution (400 ml) was frozen at −75° C.

Fraction G was biologically tested in animals detecting a FSH potency of 42.000 IU/ml and LH potency of 33.780 IU/ml. With this result, a portion of the solution (80 ml) of Fraction G was processed under conditions for separating FSH and LH (Fractions J2 and J3 respectively).

1.3 Preparation of Fractions J

1) Preparation of Fractions J2 (FSH Bioactivity) and J3 (LH Bioactivity)

Ammonium sulfate was added to an aliquot of Fraction G (80 ml) until a concentration 1 M. This solution was run in a Phenyl-Sepharose HP chromatographic column and was eluted with 2 volumes of buffer, 50 mM sodium phosphate, 1 M sulfate ammonium, pH 5.1 The elution was continued with 2 volumes of buffer, 50 mM sodium phosphate, 0.5 M ammonium sulfate, pH 5.1, and finally with 2 volumes of 50 mM sodium phosphate buffer (60% v/v) and 96% ethanol (40% v/v)

The FSH bioactive fraction was eluted with buffer, 50 mM sodium phosphate, 0.5 M ammonium sulfate, pH 5 (Fraction J2) was dialyzed and concentrated using PM 10 membrane ultrafiltration (Diaflo Ultrafilters, Amicon-Millipore), against a 50 mM sodium phosphate buffer, pH 5.7, and then was frozen at −75° C.

The LH bioactive fraction eluted with 50 mM sodium phosphate buffer (60% v/v) and 96% ethanol (40% v/v) (Fraction J3) was dialyzed and concentrated using PM 10 membrane ultrafiltration (Diaflo Ultrafilters, Amicon-Milhpore), against a 50 mM sodium phosphate buffer, pH 5.7, and then was frozen at −75° C.

Fraction J3-UP 50 mg of Fraction J3 was dialyzed against 40 mM tris buffer, pH 8.5 and loaded onto XK 16/40 column prepared with Capto-adhere (Vol 24 ml) using an ÄKTA purifier system. Gradient in different steps was used to eliminate impurities.

The sequence of buffers and elution volumes were:
40 mM tris buffer at pH 8.5+0 mM NaCl: 1 volume
40 mM tris buffer at pH 8.5+50 mM NaCl: 3 volume
40 mM tris buffer at pH 8.5+100 mM NaCl: 3 volume
40 mM tris buffer at pH 8.5+225 mM NaCl: 5 volume
40 mM tris buffer at pH 8.5+300 mM NaCl: 5 volume
40 mM tris buffer at pH 8.5+1000 mM NaCl: 3 volume Purified LH fraction (Fraction J3-UP) was obtained with 40 mM tris buffer at pH 8.5+225 mM NaCl buffer (FIG. 2). The major area under the curve of the chromatogram corresponds to LH inactive protein that elutes with 1000 mM NaCl. The LH bioactivity that is recovered in a small protein peak eluted with 225 mM NaCl strongly suggests a high purification achievement. The specific LH bioactivity was determined by bioassay (see Table 1). A purification of more than 6 times in the biopotency (from 9,400 IU LH/mg protein to 58,300 IU LH/mg protein) was achieved.

The yield of the process determined by the LH biopotency recovered in the J3-UP fraction was about 80%.

Balancing Step to Obtain HMG-UP:

Finally, to produce HMG-UP that requires a FSH:LH ratio of 1:1, a balancing step to adjust the content of both hormones was performed. Equivalent amounts of FSH bioactivity from Fraction J2 and LH bioactivity from Fraction J3-UP were mixed. The mixed solution was sterile filtrated, nanofiltrated and precipitated.

CONCLUSIONS

Urinary HMG-HP still contains non-gonadotrophin proteins as contaminants.

Multimoldalchromatography performed with a Capto-adhere resin was introduced to remove efficiently the contaminant proteins of Fraction J3 rendering a fraction called Fraction J3-UP. Non gonadotropins proteins such as plasma serine protease inhibitor, afamin, insulin-like growth factor binding protein 7, zinc alpha-2-glycoprotein and albumin were removed during the above purification method. These impurities are strongly adsorbed to the column eluting later in the chromatography. Interestingly, Fraction J3-UP shows a minor area under the curve in the chromatogram indicating the high purification degree of the LH bioactivity.

Fraction J3-UP obtained by Capto-adhere was assayed to determine its LH biopotency. The specific LH bioactivity confirms the successful purification of this hormone. The biopotency of this fraction was about 58,300 IU LH per mg of protein which represents an increase of more than 6 times of this parameter when compared to activity of Fraction J3 (9,400 IU LH per mg protein). In the same way, the two-dimensional electrophoresis confirms the high degree of purity of the Fraction J3-UP obtained by the Capto-adhere.

HMG-UP was obtained in a balancing step by mixing Fraction J2 (FSH bioactivity fraction) and Fraction J3-UP (LH bioactivity fraction).

The HMG-UP material shows a significant increase in both the FSH and LH specific biopotency. In fact, values as high as 8,200 IU per mg of protein for both FSH and LH were obtained representing an increase of almost 175% when compared to the same parameters determined in the HMG-HP material.

The characterization of the chromatographic pattern by a sensitive technique as 2D-gel confirms the higher purity grade of the HMG-UP with no other detectable impurities. Finally, the proposed manufacturing process introduces a single and simple chromatographic method able to be use in an industrial scale to increase de purity of urinary gonadotropins

REFERENCES

ASRM Practice Committee, *Gonadotropin preparations: past, present, and future perspectives*, Fertility and Sterility, 90, Suppl. 3, S13, (2008).

Bradford M M., *A rapid and sensitive method for the quantitation of microgram quantities of protein utilizing the principle of protein-dye binding*, Anal Biochem. 1976 May 7; 72:248-54 (1976).

Basset R, Lispi M, Ceccarelli D, Grimaldi L, Mancinelli M, Martelli F, Van Dorsselaer A., *Analytical identification of additional impurities in urinary-derived gonadotrophins*, Reproductive BioMedicine Online Vol 19. No. 3, 300-313 (2009).

Hartree E F, *Determination of Proteins: A modification of the Lowry Method that gives a linear photometric response*, Anal Biochem 48: 422-427, (1972).

Hellman U. *Sample preparation by SDS-PAGE and in-gel digestion*, In Jollès P, Jörnvall H (Eds). *Proteomics in functional genomics. Protein structure analysis*. Basel, Switzerland: Birkhäuser Verlag. 43-54 (2000).

Kuwabara Y, Mine K, Katayama A, Inagawa T, Akira S, Takeshita T., *Proteomic analyses of recombinant human follicle-stimulating hormone and urinary-derived gonadotropin preparations*, J Reprod Med. August; 54(8): 459-66 (2009).

Lispi M, Basset R, Crisci C et al. *Comparative assessment of the consistency and quality of a highly purified FSH extracted from human urine (urofollitropin) and a recombinant human FSH (follitropin alpha)* Reproductive BioMedicine Online 13, 179-193, (2006).

Lowry O H, Rosebrough N J, Farr A L, Randall R J., *Protein Measurement with the Folin Fenol Reagent*, J Biol Chem. 193(1):265-75 (1951).

Van de Weijer Berthm, Mulders John, Bos Ebo, Verhaert Peter, Van den Hooven Henno W., *Compositional analyses of human menopausal gonadotrophin preparation extracted from urine (Menotropin). Identification of some of its major impurities*, Reproductive BioMedicine Online Vol 7. No. 5, 547-557, (2003).

EP1169349 B1, Instituto Massone S. A., 28 Mar. 2007.

The invention claimed is:

1. A process for obtaining a composition of HMG-UP (human menopausal gonadotropin with ultra-purity grade) free of non-gonadotropin contaminants, the process comprising subjecting an acidified human menopausal/postmenopausal urine composition to the following steps:
i) treating the acidified human menopausal/postmenopausal urine with kaolin, wherein gonadotropins and non-gonadotropin proteins present in the urine are adsorbed in the kaolin;
ii) eluting the gonadotropins adsorbed in the kaolin by alkaline elution, said gonadotropins being separate in a fraction;
iii) obtaining a Fraction A by precipitating the fraction containing the gonadotropins with acetone;
iv) extracting a bioactive fraction from the Fraction A with 10% w/v solution of ammonium acetate in 70% ethanol and precipitating the extracted Fraction A with 10% ammonium acetate in 90% ethanol to obtain a Fraction B;
v) purifying the Fraction B by ion-exchange chromatography to obtain a fraction C;
vi) purifying the Fraction C by cation exchange chromatography using a strong cationic resin and eluting with ammonium acetate to obtain an eluted Fraction C;
vii) obtaining a Fraction F comprising precipitating the eluted Fraction C with ethanol at an acidic pH;
viii) purifying the Fraction F by anion exchange chromatography using a strong anion resin and eluting with ammonium acetate to obtain a Fraction G;
ix) purifying the gonadotropins obtained in Fraction G using hydrophobic interaction chromatography by sequential addition of buffers which comprise a decreasing concentration of ammonium sulfate and obtaining Fractions J2 and J3, wherein Fraction J2 comprises FSH bioactivity and Fraction J3 comprises LH bioactivity;
x) purifying the Fraction J3 using a strong anion exchanger with multimodal functionality and eluting with a buffer at a constant pH by modifying the conductivity to obtain a Fraction J3-UP which only has LH activity;
xi) obtaining of a Fraction HMG-UP in a balancing step by mixing equivalent bioactivities of FSH from the Fraction J2 and LH from the Fraction J3-UP; and
xii) subjecting said fraction HMG-UP to the steps of:
a) sterile filtration,
b) nanofiltration, and
c) precipitation;
in order to obtain the HMG-UP composition free of non-gonadotropin contaminants.

2. The process according to claim 1, wherein the non-gonadotropin contaminants are selected from the group consisting of plasma serine protease inhibitor, afamin, insulin-like growth factor binding protein 7, zinc alpha-2-glycoprotein and albumin.

* * * * *